(12) United States Patent
Takats

(10) Patent No.: US 9,046,448 B2
(45) Date of Patent: Jun. 2, 2015

(54) SYSTEM AND METHOD FOR IDENTIFICATION OF BIOLOGICAL TISSUES

(75) Inventor: Zoltan Takats, Fernwald (DE)

(73) Assignee: MICROMASS UK LIMITED, Wilmslow (GB)

(*) Notice: Subject to any disclaimer, the term of this patent is extended or adjusted under 35 U.S.C. 154(b) by 553 days.

(21) Appl. No.: 13/322,343

(22) PCT Filed: May 27, 2010

(86) PCT No.: PCT/IB2010/001261
§ 371 (c)(1),
(2), (4) Date: Mar. 8, 2012

(87) PCT Pub. No.: WO2010/136887
PCT Pub. Date: Dec. 2, 2010

(65) Prior Publication Data
US 2012/0156712 A1    Jun. 21, 2012

Related U.S. Application Data

(60) Provisional application No. 61/181,421, filed on May 27, 2009.

(51) Int. Cl.
*G01N 1/02* (2006.01)
*G01N 27/62* (2006.01)
(Continued)

(52) U.S. Cl.
CPC *G01N 1/02* (2013.01); *G01N 27/62* (2013.01); *G01N 2001/028* (2013.01); *G01N 2001/045* (2013.01); *G01N 2001/2886* (2013.01); *H01J 49/04* (2013.01)

(58) Field of Classification Search
None
See application file for complete search history.

(56) References Cited

U.S. PATENT DOCUMENTS 3,479,545 A    11/1969  Wilson et al.
4,935,624 A *   6/1990  Henion et al. ............... 250/288
(Continued)

FOREIGN PATENT DOCUMENTS

EP    1 855 306    11/2007
JP    2004-264043   9/2004
(Continued)

OTHER PUBLICATIONS

Tottszer et al., "Laser heating versus resistive heating in the field-desorption mass spectrometry of organic polymers," J. Phys. D: Appl. Phys. 1988, 21:1713-1720.*
(Continued)

*Primary Examiner* — Samuel Woolwine
*Assistant Examiner* — Kaijiang Zhang
(74) *Attorney, Agent, or Firm* — Knobbe, Martens, Olson & Bear, LLP

(57) ABSTRACT

The present invention provides for a system, method, and device for analyzing, localizing and/or identifying tissue types. The method includes analyzing, localizing and/or identifying one or more tissue samples, characterized in that the method comprises: (a) generating gaseous tissue particles from a site in the one or more tissue samples, (b) transporting the gaseous tissue particles from the site to an analyser, (c) using the analyser for generating tissue-related data based on the gaseous tissue particles, and (d) analyzing, localizing and/or identifying the one or more tissue samples based on the tissue-related data. The invention can either be used in close conjunction with a surgical procedure, when one or more surgical tools are an integrated part of ionization, or as a separate mass spectrometric probe for the analysis of one or more tissue parts.

14 Claims, 11 Drawing Sheets

(51) Int. Cl.
*C12Q 1/02* (2006.01)
*H01J 49/00* (2006.01)
*B01D 59/00* (2006.01)
G01N 1/04 (2006.01)
G01N 1/28 (2006.01)
H01J 49/04 (2006.01)

(56) References Cited

U.S. PATENT DOCUMENTS

| | | | |
|---|---|---|---|
| 5,559,326 A | 9/1996 | Goodley et al. | |
| 5,869,344 A * | 2/1999 | Linforth et al. | 250/288 |
| 6,531,318 B1 | 3/2003 | Palmer Toy et al. | |
| 6,825,464 B2 | 11/2004 | De La Mora | |
| 6,838,663 B2 | 1/2005 | Coon et al. | |
| 7,161,144 B2 | 1/2007 | Syage et al. | |
| 7,335,897 B2 | 2/2008 | Takats et al. | |
| 7,564,028 B2 | 7/2009 | Vestal | |
| 7,687,772 B2 | 3/2010 | Shiea | |
| 7,928,364 B2 | 4/2011 | Musselman | |
| 8,203,117 B2 | 6/2012 | Wiseman et al. | |
| 8,286,260 B2 | 10/2012 | Vertes et al. | |
| 8,314,382 B2 | 11/2012 | Takats | |
| 8,324,570 B2 | 12/2012 | Wiseman et al. | |
| 2002/0008871 A1 | 1/2002 | Poustka | |
| 2002/0070338 A1 | 6/2002 | Loboda | |
| 2002/0076824 A1 | 6/2002 | Haglund, Jr. et al. | |
| 2003/0008404 A1 | 1/2003 | Tomita et al. | |
| 2003/0119193 A1 | 6/2003 | Hess et al. | |
| 2003/0193023 A1 | 10/2003 | Marsh | |
| 2004/0007673 A1 | 1/2004 | Coon et al. | |
| 2004/0124352 A1 | 7/2004 | Kashima et al. | |
| 2004/0235395 A1 | 11/2004 | Hashish et al. | |
| 2005/0017091 A1 | 1/2005 | Olsen et al. | |
| 2005/0032471 A1 | 2/2005 | Pfarr et al. | |
| 2005/0072916 A1 | 4/2005 | Park | |
| 2005/0074361 A1 | 4/2005 | Tanoshima et al. | |
| 2005/0077644 A1 | 4/2005 | Bryan et al. | |
| 2005/0138861 A1 | 6/2005 | O'Connor | |
| 2005/0154490 A1 | 7/2005 | Blaine et al. | |
| 2005/0159765 A1 | 7/2005 | Moutafis et al. | |
| 2005/0178962 A1 | 8/2005 | Guevremont et al. | |
| 2005/0230635 A1 | 10/2005 | Takats et al. | |
| 2005/0258358 A1 | 11/2005 | Thakur | |
| 2006/0035570 A1 | 2/2006 | Chisum et al. | |
| 2006/0091308 A1 | 5/2006 | Boyle et al. | |
| 2006/0097084 A1 | 5/2006 | Gromer et al. | |
| 2006/0108539 A1 | 5/2006 | Franzen | |
| 2006/0186334 A1 | 8/2006 | Jolliffe et al. | |
| 2006/0250138 A1 | 11/2006 | Sparkman et al. | |
| 2006/0255264 A1 | 11/2006 | Belford | |
| 2007/0023631 A1 | 2/2007 | Takats | |
| 2007/0023677 A1 | 2/2007 | Perkins et al. | |
| 2007/0110666 A1 | 5/2007 | Pevsner et al. | |
| 2007/0114437 A1 | 5/2007 | Kovtoun | |
| 2007/0176113 A1 | 8/2007 | Shiea | |
| 2008/0001081 A1 | 1/2008 | Jindai et al. | |
| 2008/0067352 A1 | 3/2008 | Wang | |
| 2008/0149822 A1 | 6/2008 | Vertes et al. | |
| 2008/0172075 A1 | 7/2008 | Ammann | |
| 2008/0173809 A1 | 7/2008 | Wu | |
| 2008/0234579 A1 | 9/2008 | Halevy-Politch et al. | |
| 2008/0262321 A1 | 10/2008 | Erad et al. | |
| 2009/0065714 A1 | 3/2009 | Keady | |
| 2010/0078550 A1 | 4/2010 | Wiseman et al. | |
| 2010/0096546 A1 | 4/2010 | Ewing et al. | |
| 2010/0280409 A1 | 11/2010 | Mark | |
| 2011/0215233 A1 | 9/2011 | Vertes et al. | |
| 2012/0112057 A1 | 5/2012 | Musselman | |

FOREIGN PATENT DOCUMENTS

| | | |
|---|---|---|
| JP | 2005-527786 | 9/2005 |
| JP | 2005-539199 | 12/2005 |
| JP | 2007-513695 | 5/2007 |
| JP | 2007-170870 | 7/2007 |
| JP | 2008-147165 | 6/2008 |
| JP | 2009-539093 | 11/2009 |
| JP | 2009-539114 | 11/2009 |
| JP | 2012-505519 | 3/2012 |
| WO | WO 85/04093 | 9/1985 |
| WO | WO 2005/094389 | 10/2005 |
| WO | WO 2006081240 A1 * | 8/2006 |
| WO | WO 2007/138371 A2 | 12/2007 |
| WO | WO 2007/140351 A2 | 12/2007 |
| WO | WO 2009/157312 A1 | 12/2009 |

OTHER PUBLICATIONS

Takats et al., "Characterization of DESI-FTICR mass spectrometry—from ECD to accurate mass tissue analysis," J. Mass Spectrom. 2008, 43:196-203, published online Oct. 8, 2007.*
McEwen et al., "Analysis of Solids, Liquids, and Biological Tissues Using Solids Probe Introduction at Atmospheric Pressure on Commercial LC/MS Instruments," Anal. Chem. 2005, 77:7826-7831.*
Lee et al., "Thermally Assisted Electrospray Interface for Liquid Chromatography/Mass Spectrometry," Rapid Commun. Mass Spectrom. 1992, 6:727-733.*
Sakairi et al., "Characteristics of a Liquid Chromatograph/Atmospheric Pressure Ionization Mass Spectrometer," Anal. Chem. 1988, 60:774-780.*
Australian Office Action dated Dec. 10, 2013, from Australia Patent Application No. 2010252652 (3 pages).
Down, S., "A DESI-rable ionization revolutionizes mass spectrometry", Base Peak, Aug. 15, 2005.
Liang Qiao et al., "Electrostatic-Spray Ionization Mass Spectrometry," *Analytical Chemistry*, vol. 84, No. 17, Sep. 4, 2012, pp. 7422-7430.
PCT International Search Report and Written Opinion for International Appln No. PCT/IB2012/003009, dated Aug. 14, 2013, 6 pages.
PCT International Search Report for International Appln No. PCT/IB2010/001261, dated Sep. 21, 2010, 5 pages.
Takats, Z. et al., "Mass spectrometry Sampling under Ambient Conditions with Desorption Electrospray Ionization", Science, Oct. 15, 2004, vol. 306.
International Search Report, for International Application No. PCT/IB2012/002995, date of mailing: Sep. 10, 2013 (3 pages).
Written Opinion of the International Searching Authority, for International Application No. PCT/IB2012/002995, date of mailing: Sep. 10, 2013 (6 pages).
English Translation of Japanese Office Action, Japanese Patent Application No. 2012-512467, mailing date: Nov. 5, 2013.
Barrett, William L., and Shawn M. Garber. "Surgical smoke: a review of the literature." Surgical endoscopy 17.6 (2003): 979-987.
Al Sahaf, O. S., et al. "Chemical composition of smoke produced by high-frequency electrosurgery." Irish journal of medical science 176.3 (2007): 229-232.
Moot, et al. "Composition of Volatile Organic Compounds in Diathermy Plume as Detected by Selected Ion Flow Tube Mass Spectrometry," ANZ Journal of Surgery, 2007, vol. 77, pp. 20-23 in 4 pages.

* cited by examiner

SYSTEM AND METHOD FOR IDENTIFICATION OF BIOLOGICAL TISSUES

RELATED PRIORITY APPLICATIONS

This Application is a U.S. National Phase patent application of the PCT International Application No. PCT/AB2010/001261 filed on May 27, 2010, designating the United States and published on Dec. 2, 2010 as WO 2010/136887, which claims the benefit of the filing date of U.S. Provisional Application No. 61/181,421, filed May 27, 2009. The disclosures of each of these prior applications are incorporated by reference in their entirety and should be considered part of this specification.

FIELD OF THE INVENTION

The present invention relates to devices, systems and methods for analyzing, localizing and/or identifying tissues. More specifically, the present invention relates to devices, systems and methods for analyzing, localizing or identifying tissues in real time and in situ by combining disintegration of tissues and an analytical method such as mass spectrometry.

BACKGROUND OF THE INVENTION

Throughout this application, various references are cited in square brackets to describe more fully the state of the art to which this invention pertains. The disclosure of these references is hereby incorporated by reference into the present disclosure.

Identification of pathological or abnormal tissues has crucial importance during the diagnosis and treatment of malignant processes. Generally, cancer is diagnosed based on information obtained by using imaging methods. Certain imaging methods (CT, MRI) do not provide sufficient information for the identification of malignant proliferations, but give high resolution imaging. Other methods, especially nuclear imaging techniques provide relatively poor resolution, however, easily identify proliferating tissue parts, including various types of cancer. Thus, combinations of two types of imaging methods (PET/CT, PET/MRI) are used for the identification and proper localization of cancer.

Accurate diagnosis is generally obtained by histology or cytology. Histology is the gold standard method for abnormal/pathological tissue identification, hence tissue classification is based on histological examination of tissue specimens. Histology traditionally involves the following steps: (1) sampling (biopsy or surgery), (2) Fixation of sample using mainly formalin, (3) Processing or embedding sample into solid matrix, (4) sectioning to obtain 2-10 µm thick sections, (5) staining and (6) visual examination of sections under microscope. Staining fundamentally determines the type of information obtained. Traditional stains (e.g. eosin-hematoxylin) enable identification of cells based on morphological features, while immunohistochemical staining reveals the presence of certain proteins in cells.

As an alternative to histology/histopathology, cytopathological methods are also widely used. In case of cytopathology, only cells are taken as sample, from either biological fluids or directly from bulk tissue (aspiration cytopathology) and samples, similarly to histology, are examined under microscope after proper staining procedure.

Both histopathology/cytopathology and imaging methods are successfully used for diagnosis of cancer and follow-up of anti-cancer therapy. However, in contrast to the amount of information available before and after surgery, there is only little information available for the surgeon about the actual position of malignant tissue relative to visible features on surgical site. In the general case, surgeon relies on pre-operative imaging and his/her own senses, with special regard to tactility and vision.

The problem of positioning the malignant tissue has been traditionally solved by intra-operative histopathological examination of removed tumour. This is performed by freezing the freshly removed tissue, and sending it to pathology lab, where sample is sectioned, stained and examined under microscope. The aim of the procedure is to find out whether all the borders of removed tissue are "clear" (i.e. only healthy tissue was dissected) or not. Although the procedure is used widely, it has number of disadvantages, including about 20 minutes time demand, while the patient is in the operating room with open an surgical wound, and low reliability of the results caused by sub-optimal processing of samples.

Further methods developed for intra-operative localization of tumours include the utilization of various imaging methods during surgery. Sonography and X-ray fluoroscopy has long been used to follow surgical procedure, though their application generally causes interruption of the surgical intervention. Recently, special imaging systems based on MRI and CT have been developed for providing real-time information for surgeons. Intra-operative imaging systems have recently been equipped with navigation, which helps to link images to visually observable features. Although these systems were proven to be extremely useful in certain applications, e.g. spinal surgeries, they are not capable of identifying minor amounts of tumour tissue on surgical area or minor proximal metastases.

A promising group of recently developed technologies employs selective chemical labelling of malignant tissue. Labelling molecules carry either radionuclides or fluorescent moieties. Since proliferating cells accumulate these molecules, they can be visualized either with a gamma camera or an infrared camera for example. These methods are successfully used for detection of proximal metastases, e.g. detection of so-called sentinel lymph nodes that accumulate tumour cells close to primary tumours. Weakness of these methods lies in their selective nature to certain tumours, their incompatibility with surgical techniques and the undesired side effects of labels. It has to be noted, that melanoma can be detected by means of near-infrared two photon laser induced fluorescence without labeling, however this technique can only be used for detection of primary melanoma on skin surface.

Malignant tumours can be generally differentiated from healthy tissues based on their accelerated metabolism. Tumour cells accumulate basic nutrients or molecules that are similar to these basis nutrients (e.g. fluorodesoxyglucose-FDG). When these nutrients or fake nutrient molecules are labelled with radionuclide (18FDG in PET) or fluorescent moiety, tumour becomes visible using appropriate visualization method. Besides accelerated metabolism, tumours are different from healthy cells in a number of different ways. Tumours, for example show markedly different chemical composition from the distribution of small metabolic constituents to different protein expression and post-translational modification patterns. These chemical features can be used in immunohistochemical visualization of tumours, and also in chemical imaging of tissue sections using infrared spectrophotometry or mass spectrometry. Among these methods, mass spectrometry is the sole technique which can be the basis of an in-situ, in-vivo tissue identification tool utilizing the different chemical composition of different tissues.

Mass spectrometric ionization methods have been traditionally developed for the analysis of gaseous or volatile materials. One disadvantage of these ionization methods is that they lack the capability of analysis of non-volatile compounds. This group of compounds includes peptides, proteins, nucleic acids, carbohydrates, etc.; that is approximately 90% of biologically relevant molecules.

From the 1970's, a new family of ionization methods has been developed, which was able to convert condensed phase molecules directly into ions on the gas/solid or gas/liquid interface, and subsequently desorb the nascent ions from the surface. These ionization methods are generally termed as 'desorption ionization' methods.

Second generation of desorption ionization methods employed an alternative way of ionization by utilizing a so-called analytical beam for ionization. Analytical beam comprises high energy particles (atoms, molecules, atomic or molecular ions, photons, etc.) which are directed onto the surface of the sample. Impact of the analytical beam on the surface produces micro-explosions yielding gaseous ions and molecules of surface material. An early method utilizing analytical beam was plasma desorption ionization which employed high energy particles produced by radioactive decay of californium isotopes [Macfarlane R D, et al. Science, 191 (4230), 920-925. 1976].

While plasma desorption utilized a divergent beam of poorly defined species, secondary ion mass spectrometry (SIMS) employed a collimated beam of atomic or cluster ions accelerated by static electric fields into the range of 10-30 keV [Bennighoven, A, Surface Science 28(2) 541-1971]. SIMS is capable of reaching as good as 10 nm spatial resolution, due to the cross section of focused ion beams. In spite of the excellent spatial resolution, widespread application of SIMS is strongly hindered by limited molecular weight range of molecules, which undergo SIMS ionization. Generally molecules having molecular weight below 1 kDa can be detected by means of SIMS, however there is a strong discrimination against heavier ions even in this narrow mass range. Method can also be used for in-depth analysis (dynamic SIMS) however in this case the higher energy ion beam produces mainly atomic ions. Investigation of liquid samples has also been developed in the case of SIMS ionization. (liquid SIMS; LSIMS) [Aberth, W, Analytical Chemistry, 54 (12): 2029-2034 1982]. Liquid-SIMS has numerous advantages compared to the original technique, including wider mass range (MW<10 kDa), better reproducibility and sensitivity. One disadvantage of LSIMS is that samples have to be dissolved in glycerol or nitrobenzyl-alcohol prior to analysis. This step often involves solubility problems, and dissolution of solid samples obviously excludes any kind of spatially resolved analysis. Further disadvantages include the milder, but still existing limitation on molecular weight of species ionized this way.

The LSIMS method was further developed by substituting the primary ion beam with a beam of high velocity noble gas atoms. This latter technique was termed 'fast atom bombardment' (FAB) and had incremental advantages compared to LSIMS [Williams, D H et al, JACS, 103 (19): 5700-5704 1981], however the method kept practically all disadvantages of the original method, including strong limitations on molecular weight and loss of capability of spatially resolved analysis.

Another direction of development of the SIMS technique was to increase the mass of projectile (primary) ions. Eventually this research has led to the development of so-called massive cluster impact (MCI) ionization which utilizes multiply charged liquid (usually glycerol) droplets as projectiles in a SIMS-like experimental setup [Mahoney, J F Rapid Communications in Mass Spectrometry, 5 (10): 441-445 1991]. Droplets are accelerated to 2-10 keV/charge and high energy droplet beam is directed onto surface carrying sample material, which can be both in solid or liquid form. Substantial advantage of MCI compared to SIMS is the further extended mass/charge range and even more importantly the fact that MCI produces predominantly multiply charged ions of macromolecular species such as proteins. This advantage allows obtaining detailed mass spectrometric information, for example sequencing of proteins. MCI still carried the disadvantage of limited molecular weight range, complicated instrumentation and cross contamination between samples due to sputtering effect of impacting glycerol droplets. Although the method is theoretically capable of spatially resolved analysis, known prior art attempts to develop this capability have all failed.

A common disadvantage of the described methods is that they generally work strictly under high vacuum conditions. Hence, samples are introduced into the high vacuum regime of mass spectrometers, which involves strong restrictions on the composition and geometry of samples, and also requires special sample introduction systems.

Laser desorption ionization methods have been developed from the early 1980's [Cooks, R G et al. JACS, 103 (5): 1295-1297, 1981]. Simple laser desorption ionization, similarly to SIMS, gives poor ionization efficiencies and they can only be used for the investigation of a relatively limited number of molecules. Laser desorption methods were revolutionized by the application of so-called matrix compounds. Matrix compounds are generally mixed to samples in solution phase and co-crystallized onto a sample carrying target surface. Since the matrix compound is used in excessive amounts, the resulting sample consists of matrix compound crystals with analyte molecules embedded into its crystal lattice. Utilization of matrix compounds increases ionization efficiencies dramatically, and also extends the area of applicability of these methods. Matrix-assisted laser desorption ionization (MALDI) [Karas, Hillenkamp, Analytical Chemistry, 60 (20): 2299-2301, 1988] is widely used for intact protein analysis and for protein identification based on the MS investigation of tryptic digests, besides polymer, nucleic acid and carbohydrate analysis. Main disadvantages of MALDI include the low ion yield, production of predominantly singly charged ions and the fact that natural surfaces can only be investigated after deposition of matrix compounds.

Need for desorption ionization methods working under atmospheric conditions has been raised recently. Advantages of atmospheric pressure desorption ionization method include: (1) Samples are not introduced into vacuum regime of mass spectrometer, which makes analytical procedure faster and more flexible, (2) since the sample does not enter vacuum, there is no need for the removal of volatile components, such as water, (3) arbitrary objects can be investigated/analyzed this way, (4) biological systems including living organisms can be investigated in an in-vivo and in-situ manner, which feature allows the application of these methods for in situ tissue identification. Desorption ionization methods utilizing collimated beam of atoms, ions, molecules, or molecular clusters cannot be used under atmospheric pressure conditions, since particles cannot be accelerated to suitable velocities at high pressure due to consecutive collisions with gas molecules. Same phenomenon is also responsible for the extreme divergence of particle beams at higher pressures, which also hinders the formation of practical analytical beams.

Among the above described methods, only laser desorption ionization can be implemented at atmospheric pressure without dramatic changes in instrumentation, since laser beams do not interact with air molecules under the conditions of ionization. Atmospheric pressure MALDI was developed by Laiko et al. (2000), *Anal. Chem.*, 72, pages 652-657; however the technique did not gain popularity due to low ion yield which problem is further increased by the 99% ion loss in atmospheric interface, and workplace safety issues generally associated with the use of laser in open experimental setups.

The recently developed desorption electrospray ionization (DESI) [Takats et al, Science, 2004] is taxonomically/phenomenologically the atmospheric pressure version of MCI technique described above. Both methods employ multiply charged solvent droplets as analytical beam, however in the case of DESI droplets are produced by electrospray and accelerated by supersonic gas stream instead of electrostatic field gradient. Nevertheless, DESI has fulfilled all expectations associated with atmospheric pressure desorption ionization methods, so it opened the door to the mass spectrometric analysis of arbitrary objects with regard to chemical composition, size and geometry. In the course of the DESI process, high velocity electrosprayed droplets impact with the sample surface. Impacting droplets dissolve molecules present on the surface, and emit secondary droplets which are charged. Charged secondary droplets carrying surface material produce ions finally following the well-known mechanisms of electrospray ionization.

Investigation of tissues by means of mass spectrometry has been pursued in two, fundamentally different ways. One approach was focused on the systematic characterization of compound groups present in tissues, while the other strategy concentrated on the fast, direct MS fingerprinting of tissues. Methods belonging to the first group generally start with homogenization and lysis of large amount of tissue, followed by selective extraction of compound group of interest (e.g. proteins or phospholipids, etc.). Compounds are separated by means of electrophoresis or chromatography, and then detected by mass spectrometry. Although these methods cannot be used for fast identification of tissues, they provide invaluable information on marker molecules characteristic to one or another type of tissue.

Fast mass spectrometric fingerprinting of tissues is generally achieved by desorption ionization methods described above. SIMS analysis of tissues gives characteristic spectra showing mainly phospholipid fragments, however, the technique works exclusively under high vacuum conditions, and hence it cannot be applied for in vivo analysis of tissues. MALDI analysis of tissue samples gives spectra featuring either ions of abundant proteins, or ions of common membrane lipids, depending on type of matrix compounds employed. Although both types of spectra are characteristic, and show unique features in case of malignant tumours, the method still cannot applied for in vivo analysis, since deposition of matrix compounds is incompatible with living organisms. Direct laser desorption ionization using infrared laser (Er-YAG or CO2) is a special case of MALDI, where water content of sample acts as matrix. This method is fully compatible with in vivo analysis (these infrared lasers are widely used in surgery), however tissue identification in this case has not been demonstrated until now. Recently developed DESI methods give spectra featuring various membrane lipids, which give characteristic patterns for a number of tissues. DESI analysis does not require any sample preparation, unlike MALDI, thus freshly cut surfaces of living tissue can be investigated. DESI analysis of living tissues, however, does not yield conclusive data, due to interference from blood and interstitial fluid leaking from surface being investigated. Further disadvantage of DESI analysis is the safety concern associated with the use of 4-5 kV DC in proximity of living organisms.

From the above analysis of the state of the art in MS it can be concluded that both abundant proteins and phospholipids give characteristic distribution in DI mass spectra of various tissues, however for in vivo MS analysis there is no appropriate ionization method developed yet.

Ionization of condensed phase, non-volatile samples via rapid heating has been pursued since the late 1960's. Rationale of this effort was to employ sufficiently high heating rate to achieve disintegration rates comparable to rate of decomposition of analyte molecules. Friedman et al. have described successful ionization of amino acids and peptides by rapid heating in the early 1970's. Assumed mechanism of these experiments was associated with the direct disintegration of ionic species present in solid phase. Experimental implementation of these experiments was limited to contact heating of pure, crystalline analyte compounds. The search for more efficient methods of heating has led to application of lasers in mass spectrometric ion sources, and eventually to the development of various laser desorption ionization methods (including MALDI) described above.

Alternatively to laser heating, thermally assisted spray disintegration of solution phase compounds have also been studied (see for example Vestal et al, *Anal. Chem.* (1980), 52, pages 1636-1641. Since spray disintegration in a vacuum or inert atmosphere dramatically increases the rate of disintegration, intact molecular species were successfully transferred to gas phase this way. These methods were termed "thermospray" and were widely used in the late 1980's and early 1990's as HPLC-MS interfaces. Most thermal disintegration methods result in the formation of overwhelmingly neutral species; hence these methods were often combined with post ionization techniques. Post ionization has been traditionally carried out via electron impact (EI) or chemical ionization (CI). Recently, a similar approach has been introduced utilizing electrospray post-ionization of gaseous species obtained by laser ablation of samples (LAESI).

What is needed is an MS-based device, system and method which can be used for direct, in situ investigation of biological tissues, that does not harm organisms being investigated and gives mass spectra characteristics to different types of tissues in a relatively short timeframe, and that also can be used in the operating room, advantageously as an integrated part of one or more surgical tools or dissecting tools.

SUMMARY OF THE INVENTION

The present invention provides for novel devices, systems and methods for analyzing, localizing or identifying tissue types. The novel devices, systems and methods of the present invention are capable of providing in situ investigation of biological tissues that do not harm organisms being investigated, and are capable of providing real-time feedback during procedures on the tissue, such as surgical procedures. The devices, systems and methods of the present invention can either be used in close conjunction with a surgical procedure for example, when one or more surgical tools are an integrated part of ionization, or as a separate mass spectrometric probe for the analysis of one or more tissue parts of a surgically exposed area.

As such, in one aspect, the present invention provides a method for analyzing, localizing and/or identifying one or more tissue samples, characterized in that the method comprises: (a) generating gaseous tissue particles from a site in the one or more tissue samples, (b) transporting the gaseous tissue particles from the site to an analyser, (c) using the analyser for generating tissue-related data based on the gaseous tissue particles, and (d) analyzing, localizing and/or identifying the one or more tissue samples based on the tissue-related data.

The present invention provides also for a system for analyzing, localizing and/or identifying one or more tissue samples. Thus, in another aspect, the present invention provides for a system for analyzing, localizing or identifying one or more tissue samples characterized in that said device comprises: (a) a disintegrating device for contacting the one or more tissue samples at a site, and for generating gaseous tissue particles from the site (b) a transport means for transporting the gaseous tissue particles from the site to an analyzer, and (c) an analyser operationally coupled to the transport means, said analyser for generating tissue-related data based on the gaseous tissue particles, wherein said tissue-related data are used for analyzing, localizing and/or identifying the one or more tissue samples.

The present invention provides also for a device for analyzing, localizing and/or identifying one or more tissue samples. Thus, in another aspect, the present invention provides for a device for analyzing, localizing and/or identifying one or more tissue samples characterized in that the device comprises: (a) a disintegrating device for contacting the one or more tissue samples at a site, and for generating gaseous tissue particles from the site and (b) a transport means configured to be operably linked to an analyser, said transport means for transporting the gaseous tissue particles from the site to the analyzer.

In another aspect yet, the present invention provides for a method of mass spectroscopy data acquisition characterized in that said method comprises: (a) contacting an area of interest in a sample with a disintegrating device capable of generating gaseous sample particles, (b) transporting the gaseous sample particles from the area of interest to a mass spectrometer, and (c) using the mass spectrometer for acquiring sample-related data based on the gaseous sample particles from the area of interest.

In yet another aspect, the present invention provides for a system for real-time diagnosis of tissue characterized in that the device comprises: (a) a disintegrating device for contacting the tissue at a site, and for generating gaseous tissue particles from the site (b) a transport means for transporting the gaseous tissue particles from the site to an analyzer, and (c) an analyser operationally coupled to the transport means, said analyser configured for generating real-time tissue-related data based on the gaseous tissue particles, wherein said tissue-related data are used for diagnosing the tissue.

It should be understood that the present invention may be used for real-time analysis or identification of any biological tissue and for any purpose. The disclosure illustrates the present invention through the example of use of the described technology in connection with a surgical procedure, however, the present invention may also be used for example for analysis of meat products for health and safety purposes, analysis of biological tissue for identification of drug molecules in the tissue, analysis of biological tissue for presence of disease or infection, and so on. None of the specific examples illustrated should be read to narrow the application of the technology described.

In yet another aspect of the invention, the systems, methods, and devices of the present invention include signalling the results of the tissue identification to a user of a surgical device at a site.

Advantages

Advantages of the methods, systems and devices at surgery application include:

Application of the method, systems and devices of the present invention allows surgeons to detect, how different types of tissues are distributed over surgical area. This feature increases detection of tumour spots, increases the precision of tissue removal in case of tumour removal surgeries and removal of necrotized/ischemic tissues, and also minimizes the mass of healthy tissues removed.

The methods, devices and systems of the present invention enable the real-time, in-situ identification of tissue parts during surgery.

The methods, devices and systems of the present invention allow for automatic alerting of surgeons when malignant tissues are dissected during surgery.

Overall benefits of use of method, device and system of the present invention include:

(a) Decreased invasiveness of tissue removal surgeries, hence faster recovery rate; less surgical preparation; automatic or semi-automatic objective tissue identification;
(b) Decreased rate of cancer recurrence;
(c) Provides for an objective criterion for identifying tissue;
(d) Enables the chemical analysis of tissues both in vivo and in microscope sections;
(e) Provides information on chemical composition of tissues for researchers;
(f) Provides a methodology for the measurement of concentrations of certain molecules (e.g. drug molecules) in tissues without sample preparation;
(g) Can be applied in conjunction with so-called chemical labelling during surgery, when a patient is given such molecule, which is known to be accumulated by malignant tissues (label), and cancer cells are detected based on the presence or absence of label molecule;
(h) Enables an alternative, however destructive, way of cell identification in cytology or flow cytometry, when cells are identified based on their mass spectrometric chemical fingerprint;
(i) Enables the in situ, in vivo identification of microbial infections in infected organs and on mucous membranes;
(j) Enables the in vivo identification of circulatory/metabolic status of tissues; and
(k) Eliminates the need for intra-surgical histopathological examination of samples, thus enables shorter operation times.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

BRIEF DESCRIPTION OF THE DRAWINGS

The present invention will become more fully understood from the detailed description given herein and from the accompanying drawings, which are given by way of illustration only and do not limit the intended scope of the invention.

DETAILED DESCRIPTION OF THE INVENTION

Figure 1:
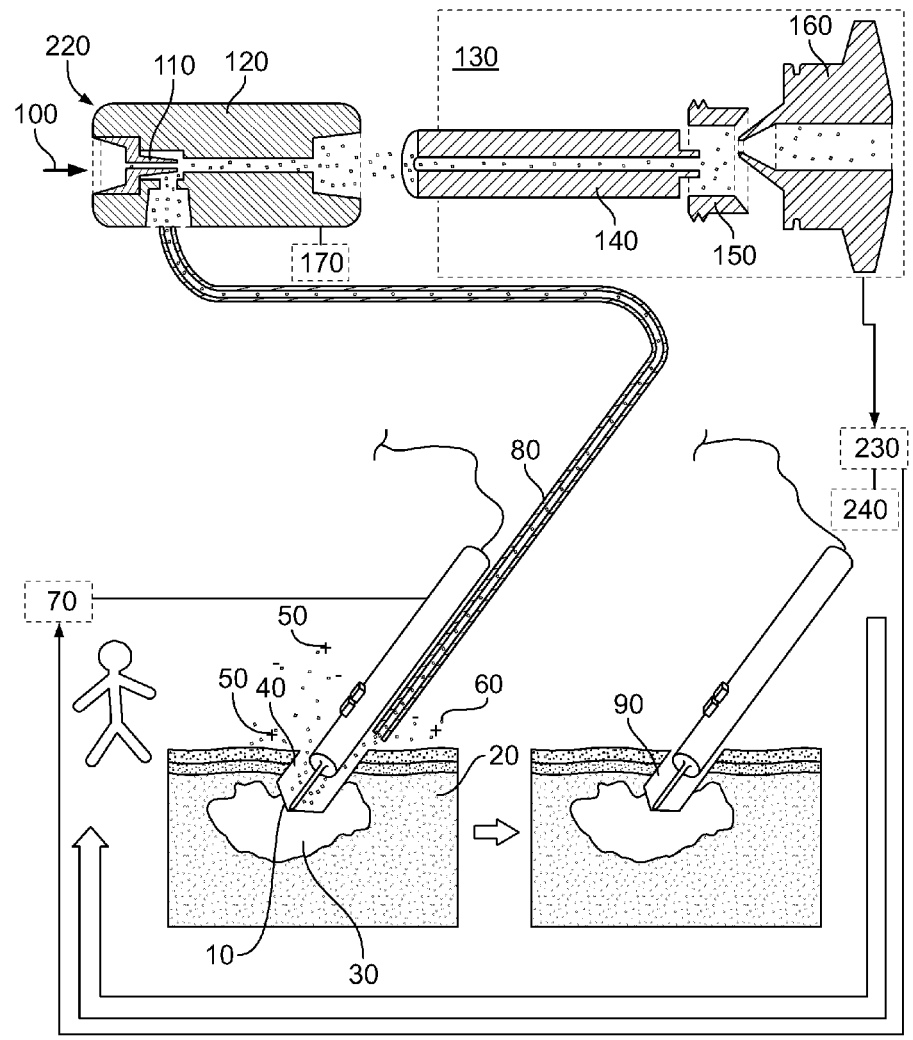
FIG. 1 illustrates a scheme of an in vivo mass spectrometric tissue identification system in accordance to one aspect of the present invention.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice-versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise.

"Area of Interest" or "Site" means an area of tissue that comprises the subject of acquired tissue-related data sets. In one embodiment, an area of interest or site is suspected of containing abnormal or pathological tissue. In some embodiments, a site is believed to contain normal tissue and the data acquired is used as control or background data.

"In situ" means the direct examination of cells or tissues. In situ includes the direct examination of tissues on a subject during a surgical procedure.

"Memory effect" can be defined as a non-linear delay between an analysis process and acquired data. A signal corresponding to one sample (sample A) may persist even when sample A is not analyzed any more, and may interfere with the analysis of a following sample B.

"Subject" or "patient" refers to an animal, including humans, in need of treatment for a condition, disorder or disease.

"Tumour tissue" refers to any neoplastic tissue including cancerous cells. The tumour tissue may be a solid tumour or a non-solid tumour, such as those present in the circulatory system, for example leukemia.

The invention will be explained in details by referring to the Figures.

The applicants discovered that surgical methods employing ultrasonic or thermal disintegration (for example electrosurgery and infrared laser surgery), produce large amounts of tissue-originated gaseous tissue particles. The applicants further discovered that mass spectra of these gaseous tissue-originated particles are similar to those obtained by other mass spectrometric techniques, such as DESI, SIMS and MALDI. As such, the present invention provides for devices, systems and methods for analyzing, localizing and/or identifying tissues in real time and in situ by combining disintegrative ionization of tissues and mass spectrometry.

By disintegrating tissue, charged and uncharged particles are generated in gas phase. The inventors discovered that the charged particles generated through disintegration manifest as clusters of molecules, which gradually undergo disassociation to yield molecular ions. This gradual disassociation typically starts at the point of disintegration and typically in connection with the present invention is completed to yield molecular icons in the mass spectrometer, preferably prior to mass analysis. Uncharged particles can be post-ionized, and post-ionization also produces a distribution of charged molecular clusters ranging from individual molecular ions to macroscopic droplets. These clusters also undergo gradual association to yield molecular ions. In this way, the disintegration of tissue is operable to yield charged tissue particles which in turn yield molecular ions suitable for use in mass spectrometry.

As such, in one aspect, the present invention provides for a system for analyzing, localizing and/or identifying one or more tissue samples characterized in that said system comprises: (a) a disintegrating device for contacting the one or more tissue samples at a site, and for generating gaseous tissue particles from the site (b) a transport means for transporting the gaseous tissue particles from the site to an analyzer, and (c) an analyser operationally coupled to the transport means, said analyser for generating tissue-related data based on the gaseous tissue particles, wherein said tissue-related data are used for analyzing, localizing and/or identifying the one or more tissue samples.

In another aspect, the present invention provides for a device for analyzing, localizing and/or identifying one or more tissue samples characterized in that the device comprises: (a) a disintegrating device for contacting the one or more tissue samples at a site, and for generating gaseous tissue particles from the site and (b) a transport means configured to be operably linked to an analyser, said transport means for transporting the gaseous tissue particles from the site to the analyzer.

The novel methods, systems and devices of the present application, termed rapid evaporative ionization mass spectrometry (REIMS) involving the aerosolization of tissue to generate and identify gaseous tissue-originated ions and to localize abnormal tissue in situ may be implemented for numerous applications. According to one embodiment, REIMS techniques can be used for diagnostic purposes to screen an area of interest to identify whether tissue of a specific type or composition, or having other specific attributes, for example cancerous tissue, is present in the area of interest and, if so, to locate the cancerous tissue with a high degree of spatial resolution. These diagnostic techniques may be used for examining an area of interest that is exposed during a surgical procedure, or an area of interest exposed to an invasive or semi-invasive instrument, such as a laparoscope, endoscope, probe, fiber optic cables, or the like. In this fashion, methods, systems and devices of the present invention may be used for fast detection and diagnosis in numerous applications, including and not limited to detection of various abnormalities, including lung cancer, cancers of the digestive system organs, including esophageal cancers, colorectal cancers, and the like; skin; reproductive organs, such as prostate, ovarian, uterine and cervical cancers, breast cancer; brain cancer; cancers of the lymphatic system and bone; and the like. Other applications of the present invention will be described below.

Basic setup of one aspect of the system of the present invention is shown in FIG. 1 in a surgical setting. The system shown in FIG. 1 comprises of following parts:

Disintegrating Device 11. A primary function of disintegrating device is to generate an aerosol out of biological tissue via either ultrasonication or rapid boiling of water content of the tissue, which disintegrates tissue structure. Disintegration leads to formation of aerosol or gaseous particles covered with surface active molecules, i.e. membrane lipids of original structures, and contain intact and thermally degraded biomolecules. These aerosol or gaseous particles may carry a net electric charge due to uneven distribution of anionic and cationic species, and these droplets can dissociate to give individual molecular ions of membrane lipids.

There are a number of different disintegration methods that can be used in the devices, systems and methods of the present invention, including ultrasonication, Joule-heating, contact heating and radiative heating, which includes electromagnetic radiation (ranging from microwave to near UV) ablation.

FIG. 1 illustrates a system wherein the disintegrating device 10 performs Joule-heating by means of inducing electric current in the tissue sample of interest. The function of electrode 10 from the point of view of analysis is to bring the biological tissue into contact with remote electric power supply 70. Electric current flowing through healthy, normal tissue parts 20 and through abnormal, pathological (such as cancer) tissue parts 30 converts tissue parts 20, 30 into a gaseous mixture of charged 50 and neutral 60 species via Joule heating. Application of high-frequency (>100 kHz) alternating current (AC) can be advantageous, because direct current (DC) and low frequency AC may interfere with the electrophysiological processes of living organisms. Thus, application of DC and low frequency AC current may be dangerous or even fatal to a subject.

Transformation of tissue constituents into corresponding gaseous tissue particles can be carried out by the presently used surgical tools including electrosurgery, laser surgery, water jet surgery, or ultrasonic surgery.

In the case of electrosurgery, for example, current density is sufficiently high only in the proximity of sharp electrodes to cause tissue disintegration; hence tissue is evaporated where a sharp electrode is in physical contact with the body. In order to eliminate additional burns, either a large area counter electrode is used (monopolar cutting) or the two sharp electrodes are close to each other (bipolar cutting). In these cases, in one aspect of the invention, a surgical device can be equipped with a transfer tube 80 and the surgical device can be converted to a bifunctional surgical and tissue identification tool.

In the case of endoscopy, standard electrosurgical, laser surgical, or ultrasonic surgical equipment can be used for sampling. Working channel of the endoscope can be used for evacuation of surgical smoke containing gaseous ions of interest. One sampling point may require the evacuation of about 1 ml of gas, hence, an applied vacuum does not result in any harmful effects.

Transfer or Transport tube 80. The transport tube 80 transfers charged and/or neutral species formed on aerosolization of tissue to an analyser, such as a mass spectrometer (MS). Since an important application of the present invention is the in situ, in vivo identification, localization and/or analysis of biological tissues 20, 30 during surgery, and mass spectrometers are immensely heavy instruments compared to surgical equipment, it is important to transfer charged 50 and/or neutral species 60 formed on tissue disintegration to a remote mass spectrometer 130 instead of placing patient to close proximity of the MS instrument. As such, in aspects of the invention the MS can be placed outside the operating room. Gas flow carrying the gaseous tissue-originated particles 50, 60 through transfer tube 80 can be generated by establishing pressure a difference between two ends of tube 80. Since pressure on sampling or tissue side of the transport tube 80 is atmospheric in most of the preferred applications (e.g. surgical applications), pressure difference can be generated by decreasing pressure at the end of tube 80 which is closer to MS 130 (MS side of transport tube 80). Pressure is decreased by employing a separate a fluid pump 220, or using the vacuum system of MS 130. Transfer tube 80 can be made of any material with sufficient mechanical strength, chemical stability and sufficiently high flexibility. For example, tube 80 can be made out of various polymers, (polyethylene, polytetrafluoroethylene, polypropylene, polyvinylchloride), metals (steel, copper), glass and fused silica. Important features of material include the lack of porosity and inertness, i.e. tube wall is not supposed to retain charged 50 and neutral 60 gaseous tissue particles and also not supposed to interact with these species 50, 60 or facilitate their chemical reactions. Internal diameter of tubing 80 can be anywhere between about 0.1 mm and about 20 mm, length of tubing can be anywhere between about 0 and about 5000 mm or of enough length to interface with the MS, wall thickness of tubing can be anywhere between about 0.01 mm and about 5 mm. Transfer tube 80 can be used at ambient temperature, or at elevated temperature. Operating temperature can be set anywhere between ambient and 400° C. Elevated temperature tends to shift adsorption-desorption equilibria taking place on wall surfaces of transfer tubing 80 towards desorption, which suppresses undesired memory effects. Elevated temperature can also shift gas-phase association-dissociation equilibria towards dissociation, which decreases the recombination rate of ionic species 50 with opposite charges. Transfer tube 80 may contain minor amounts of porous or fibrous material (glass wool, fabric, etc.) to irreversibly capture large particles not producing individual gaseous ions. It is important to note, that electrically non-conductive tubing material can only be used in such cases when ion population comprising both positive and negative ions is transferred. Ion transfer efficiency in these cases can further be improved by keeping the ions off the wall of the tubing by e.g. generating a radial pseudopotential field using RF electric fields.

It should be understood that transfer tube 80 may include a free portion that is flexible enough to permit a range of motion during use in conjunction with surgery, and a fixed portion that does not move during surgery, for reaching the remote analyser.

Transfer tube 80 can be held next to the site where the tissue is being surgically cut such that gaseous species 50, 60 can be driven into the transfer tube 80. Alternatively, the surgical tool that serves as a disintegrating device can be co-axially connected to the transfer tube 80.

Fluid Pump 220

Primary function of fluid pump 220 is to generate pressure difference along transfer tube 80 and induce gas flow through transfer tube 80. Gas flow transfers charged 50 and neutral 60 species from the site of tissue disintegration towards mass spectrometer 130. Fluid pumps employing different pumping mechanisms can be employed. However, since charged 50 and neutral 60 species can be chemically aggressive, and in the case of surgical applications fluid pump device 220 need to be disinfected or disposed after each operation, the use of Venturi gas jet pumps may be desired in these cases. A Venturi pump includes a nozzle 110 and a Venturi tube 120. Venturi pumps can dilute primary gas flow and decrease concentration of charged 50 and neutral species 60 in the gas stream, however, Venturi pumps can also focus charged 50 and neutral species 60 and facilitate their electrospray or corona discharge ionization. Further advantage of Venturi pump is the lack of moving parts which decreases the chance of malfunctioning.

Although fluid pump 220 can be omitted (as it is shown on FIG. 2), and the vacuum system of the mass spectrometer can be used as pumping system, this implementation may not be ideal in cases where large mass flow and linear velocity is required in transfer tube 80. Also, 220 fluid pump can become essential element of the system when ionization of neutral species 60 is performed at atmospheric pressure. It is important to note, that electrospray and corona discharge ionization methods can only performed at relatively higher pressures (p>10 torr).

Post Ionization Device 320

Although thermal or mechanical disintegration methods do produce charged particles 50 on the aerosolization of tissues, most of aerosolized material remains neutral in the gas phase. Furthermore, on the rapid thermal or mechanical aerosolization of tissues only certain molecules undergo ionization, which belong mainly to the group of glycerophospholipids. In order to increase ion yield, and also to increase range of molecules available for mass spectrometric analysis, ionization of neutral species 60 can be desired in certain cases. Ionization can be performed both at atmospheric pressure and in vacuum. Atmospheric pressure ionization may be preferred, since atmospheric pressure ion sources provide more stable and robust instrumental conditions and involve less serious memory effects.

Figure 3:
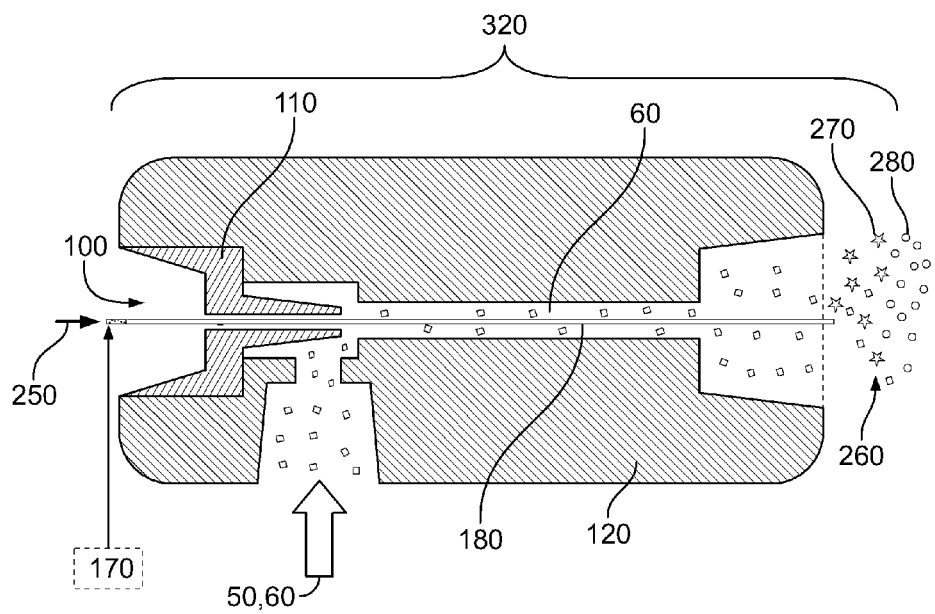
FIG. 3 illustrates the implementation of post-ionization of neutral gaseous tissue particles by means of secondary electrospray ionization.

Post ionization methods that can be used in the systems and methods of the present invention include secondary electrospray ionization depicted on FIG. 3. Secondary electrospray ionization may be implemented by placing capillary 180 through nozzle 110 of the Venturi tube 120, pumping conductive solvent 250 through capillary 180 and applying high voltage (HV) onto conductive solvent 250 by using high voltage power supply 170. By application of HV, conductive solvent 250 is sprayed 260 from ending of capillary 180 close to mass spectrometer 130, producing charged droplets 270 of conductive solvent 250. Charged droplets 270 dissolve neutral particles 60 and those charged particles 50 which carry an opposite charge, yielding charged droplets 280 containing conductive solvent 250 and molecules originated from tissue sample 20, 30. Upon the evaporation of conductive solvent 250 from charged droplets 280, gas phase ions 50 are produced, which will be subjected to mass spectrometric analysis. Advantages of secondary electrospray ionization include that this method ionizes both volatile and non-volatile molecules. Since most serious memory effects are caused by precipitation of volatile and semi-volatile molecules, which precipitations keep a low, but constant vapor pressure for these molecules in the system, analysis of non-volatile components is important from the point of view of real-time analysis.

Figure 4:
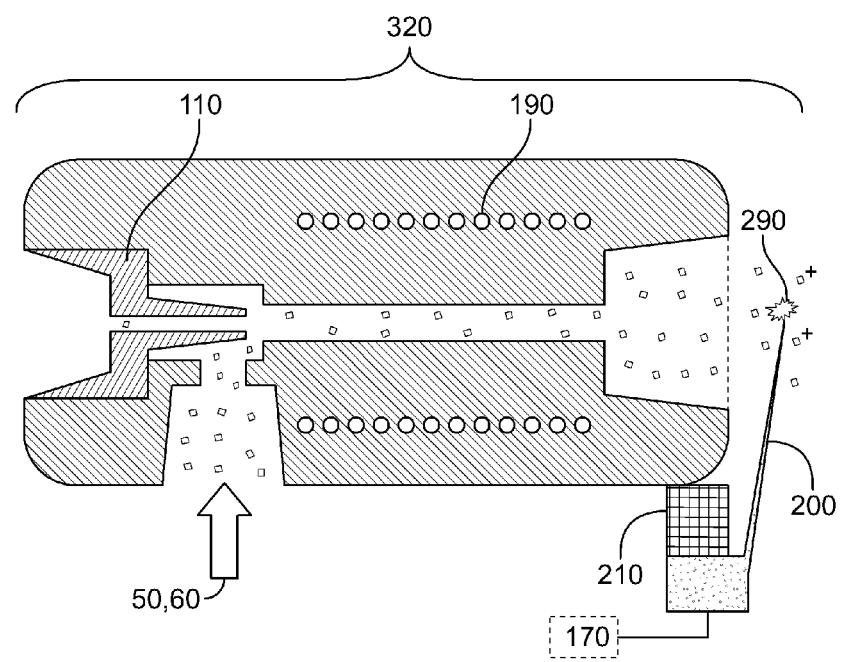
FIG. 4 illustrates the implementation of post-ionization of neutral gaseous tissue particles by means of corona discharge ionization.

Another post-ionization method that can be used in the system and methods of the present invention is corona discharge ionization, which is depicted on FIG. 4. Corona discharge is implemented by mounting discharge needle 200 onto Venturi tube 120 through needle mount 210, and applying high voltage onto needle 200 using high voltage power supply 170. In order to achieve optimal performance, Venturi tube 120 is equipped with a heater element 190 and heated to temperatures between ambient and 500° C. Although corona discharge ionizes predominantly volatile and semi-volatile molecules, corona discharge ionization can present as a more robust form of ionization than secondary electrospray ionization, and does not suffer from clogging and solubility effects. Similarily to corona discharge ionization, atmospheric pressure photoionization can also be implemented.

Ionization can also be performed under various vacuum conditions. These methods include glow discharge ionization, chemical ionization, electron capture ionization, electron impact ionization, photoionization and any ionization method which is capable of transforming molecular clusters or individual gas phase molecules into corresponding gaseous ions.

Mass Spectrometer 130

Figure 2:
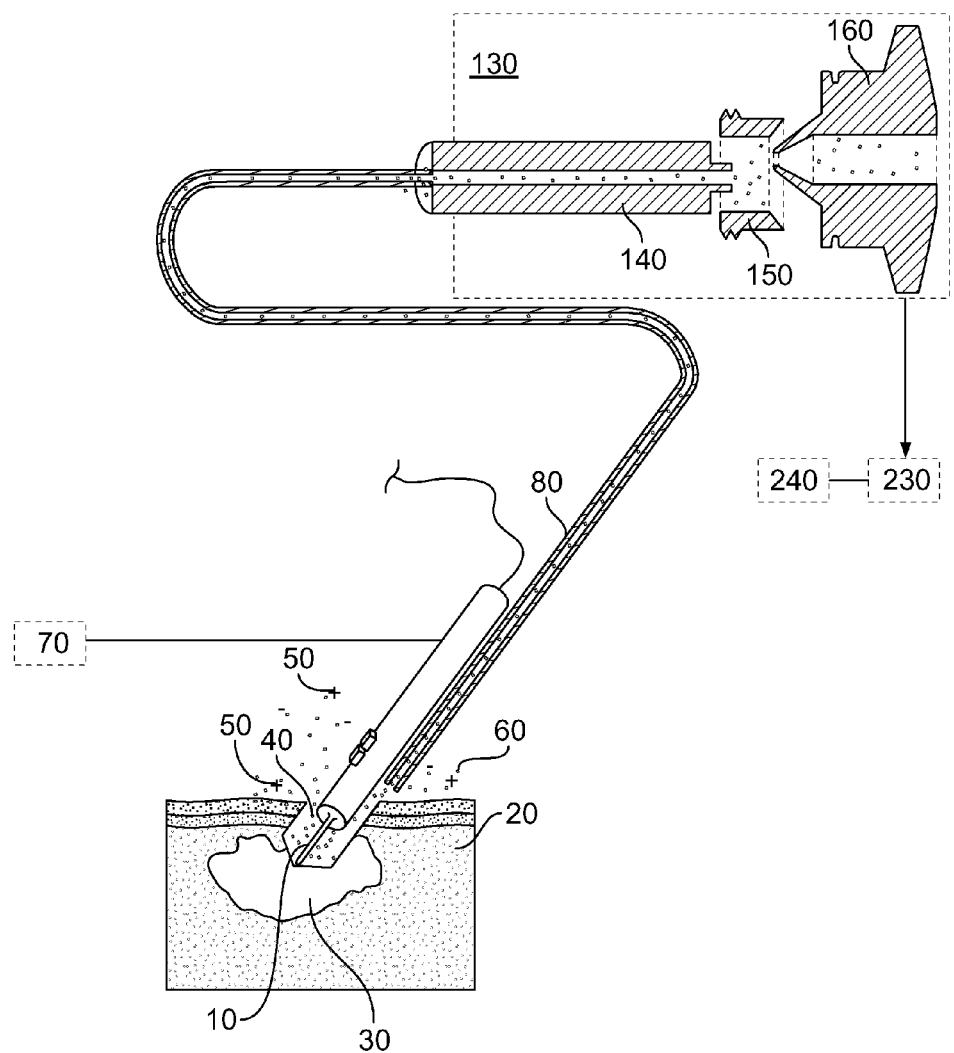
FIG. 2 illustrates a scheme of an in vivo mass spectrometric tissue identification system in accordance to another aspect of the present invention.

Function of mass spectrometer 130 is to separate and detect ions formed either directly on tissue aerosolization, or via post-ionization of neutral particles 60. Since mass spectrometers work under high vacuum conditions, instruments capable of sampling atmospheric region may be preferred for the implementation of the present invention. Atmospheric interfaces generally consist of heated capillary 140, which serves as a primary conductance limit separating atmospheric regime from a fore vacuum regime (p~1 ton) and a skimmer electrode 160 secondary conductance limit separating a fore vacuum regime from a high vacuum regime (p<$10^{-4}$ torr). The atmospheric interface depicted on FIGS. 1-3 consists of heated capillary 140, focusing lens 150 and skimmer electrode 160. The atmospheric interface setup illustrated in FIGS. 1-3 is advantageous since in this case central axes of heated capillary 140 and skimmer electrode 160 are substantially parallel but do not overlap. This way, ions 50 leaving heated capillary 140 can be deflected to the skimmer electrode 160 by applying appropriate DC potentials onto focusing lens 150. Since coulombic forces have no effect on neutral particles 60, charged particles 50 are effectively separated from neutral particles 60 and neutral particles 60 do not enter and contaminate high vacuum regime of mass spectrometer 130. Mass analyzers of any type can be applied for the mass analysis of gaseous ions 50, however so-called ion trap and time-of-flight instruments may be preferred. These mass analyzers collect ions for certain periods of time, then analyze the collected population of ions, which results in lower sensitivity of ion intensity ratios to signal transiency.

Any suitable analyzer capable of detecting gaseous tissue-originated particles 50, 60 transported by the transport tube 80 and generating tissue-related data, including a mass spectrometer or an ion mobility spectrometer, can be used in the methods, systems and devices of the present invention.

Beam of Electromagnetic Radiation 330

An alternative to disintegration of tissues via Joule-heating or via ultrasound, electromagnetic radiation (ranging from microwave to near UV) disintegration of tissues can also be utilized for obtaining tissue-originated gaseous particles, including gaseous tissue-originated ions. Beam of electromagnetic radiation 330 emitted by device 340 is adsorbed by tissues 20, 30 and energy of electromagnetic radiation beam 330 is dissipated to thermal energy which converts constituents of tissue 20, 30 into ionic and neutral gaseous species 50, 60. Application of lasers with wavelength in the infrared regime may be preferred, since in these cases only the vibrational and rotational modes of molecules are excited, thus additional photochemical reactions can be avoided. A further advantage of infrared lasers includes better absorption of infrared laser beam by tissues in comparison with visible or ultraviolet lasers. Surgical laser devices work in the infrared regime exclusively, thus commercially available laser surgical equipment can be used in the systems and methods of the present invention.

Figure 11:
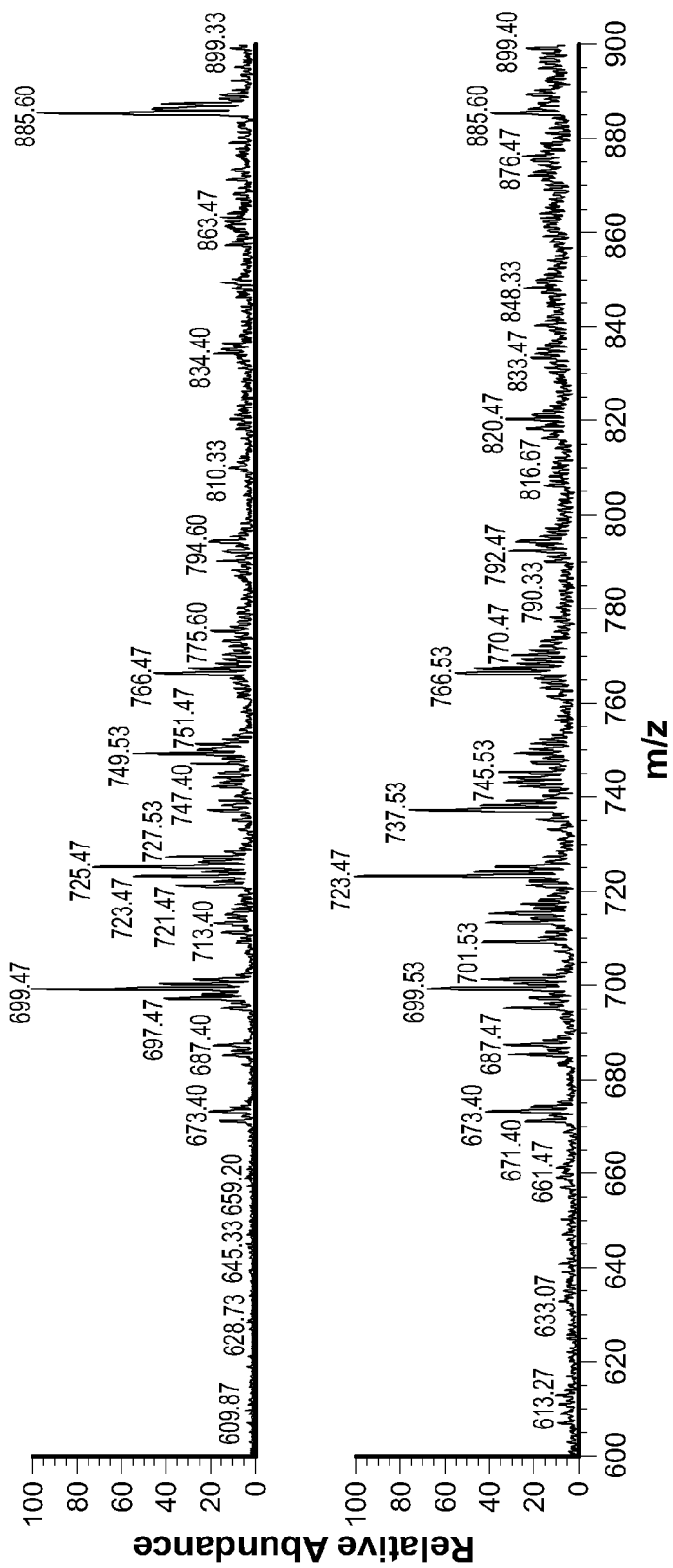
FIG. 11 illustrates a comparison between a spectrum obtained by electrosurgery (spectrum above) and a spectrum obtained by laser surgery using CO2 laser (spectrum below). Both spectra were obtained by dissecting porcine liver and analyzing the ions formed on surgical dissection without any means of post-ionization.

The surgical infrared laser can be equipped with transfer tube 80 thereby converting a surgical device into a bi-functional surgical and tissue identification tool. Disintegration of tissue occurs via rapid boiling of water content of tissues, which disintegrates tissue structure. Disintegration leads to formation of aerosol or gaseous particles covered with surface active molecules, i.e. membrane lipids of original structures, and contain intact and thermally degraded biomolecules. These aerosol or gaseous particles may carry a net electric charge due to uneven distribution of anionic and cationic species, and these droplets can dissociate to give individual molecular ions of membrane lipids, similarly to electrosurgery. Sample spectra obtained by electrosurgery and laser surgery are shown on FIG. 11.

The present invention also provides for methods developed for the mass spectrometric analysis and identification of biological tissues. General implementation of invention is depicted on FIGS. 1-3. As such, in one aspect, the present invention provides for a method for analyzing, localizing and/or identifying one or more tissue samples, characterized in that the method comprises: (a) generating gaseous tissue particles from a site in the one or more tissue samples, (b) transporting the gaseous tissue particles from the site to an analyser, (c) using the analyser for generating tissue-related data based on the gaseous tissue particles, and (d) analyzing, localizing and/or identifying the one or more tissue samples based on the tissue-related data.

The system depicted in FIG. 1 can be brought to stand-by position by turning on mass spectrometer 130, controller of tissue aerosolization device 70, and applying inert gas flow 100 onto fluid pump 220.

Using electrodes as an example of disintegrating device 10, tissue analysis can be performed by bringing electrodes 10 (that can be incorporated into a surgical device) into close contact with tissue of interest at a site, and applying potential difference between electrodes by using electric power supply 70. Upon contact of tissue 20, 30 with electrodes 10, tissue is thermally disintegrated as a result of thermal dissipation of electric energy (Joule heating), and either the whole disintegrated tissue, or a part of it, is converted into vapor 50, 60 (meaning individual molecules in gas phase) and aerosol 50, 60 (meaning clusters of molecules in gas phase)

Alternatively to electrosurgical tissue aerosolization, aerosolization of tissue parts 20, 30 by directing ultrasound, water jet or laser beam 330 onto them can also be used to generate charged 50 and neutral gaseous particles 60.

Chemical composition and electrical charging of these charged 50 and neutral gaseous particles 60 depend on factors including the type of original tissue and the method used for tissue aerosolization among number of other factors. Charged 50 and neutral gaseous particles 60 enter transport tubing 80 and are transferred to either fluid pump 220 (if a fluid pump is used), or directly to the mass spectrometer 130.

Heat-induced aerosolization of tissues can produce a considerable amount of charged particles 50, which allows tissue analysis without post cutting ionization (post-ionization) of neutral particles 60. In these cases, tube 80 can be directly connected to mass spectrometer 130, or fluid pump 220 can directly transfer (without post-ionization) charged particles 50 to mass spectrometer 130. When information obtained from mass spectrometric analysis of charged particles 50 (formed on tissue disintegration) is not sufficient for proper identification or detection of tissues, due to low signal intensity or lack of information content, post-ionization of neutral particles 60 can be used for enhancement of analytical information.

Figure 6:
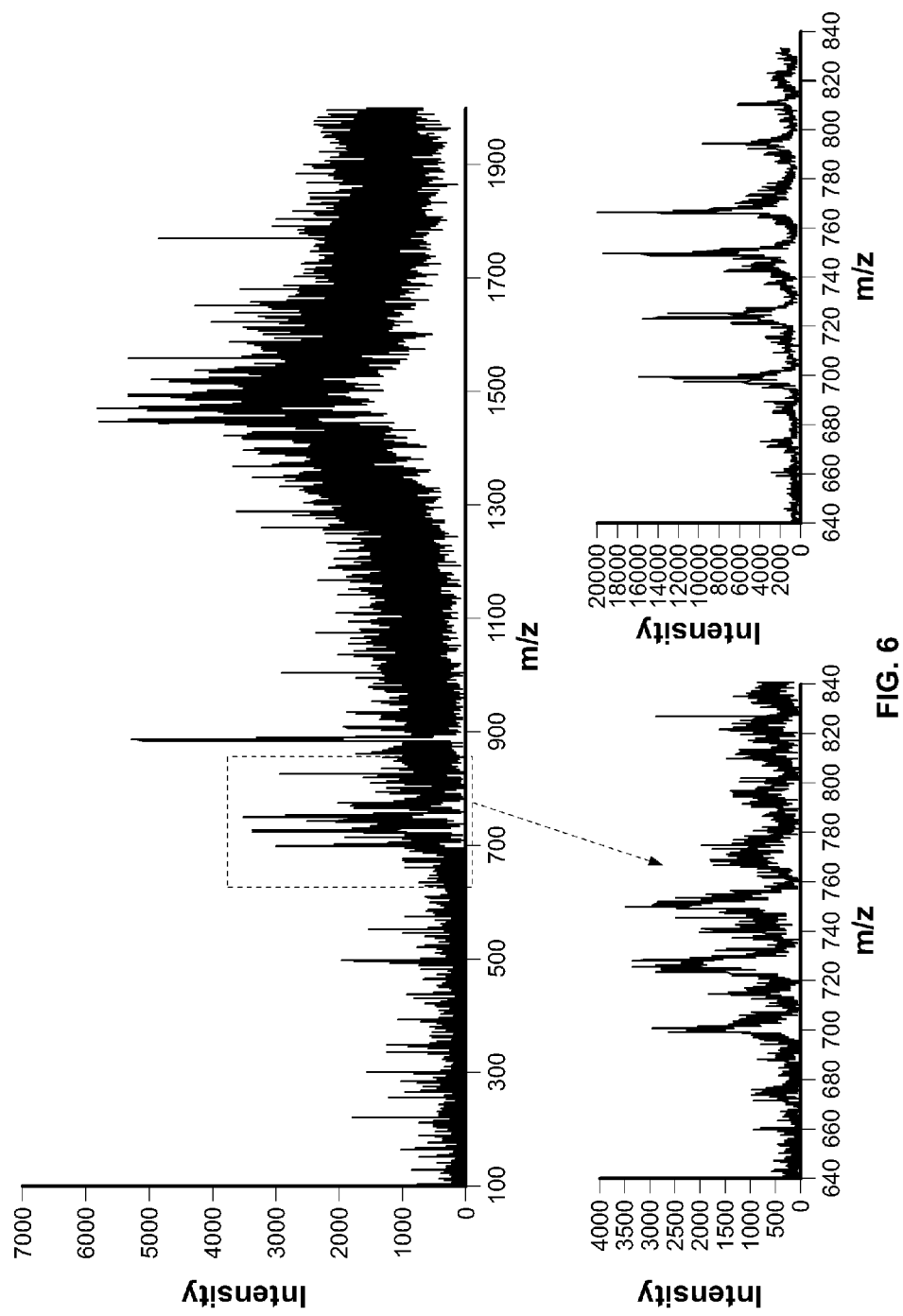
FIG. 6 illustrates a full mass spectrum obtained during electrosurgical dissection of porcine liver using the setup depicted on FIG. 1.
Figure 7:
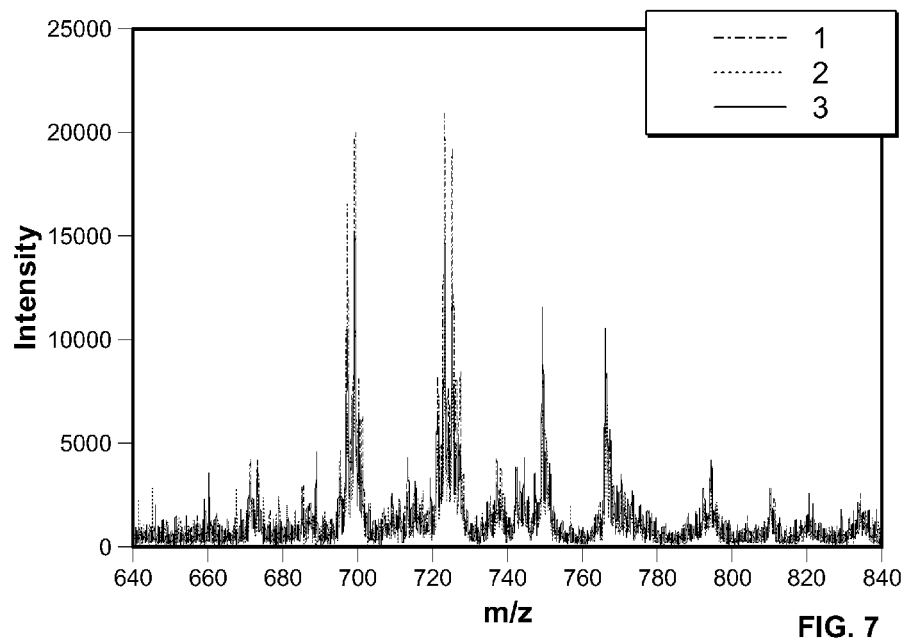
FIG. 7 illustrates three overlapping negative ion mass spectra obtained during electrosurgical dissection of porcine liver using the set up of FIG. 1.
Figure 8:
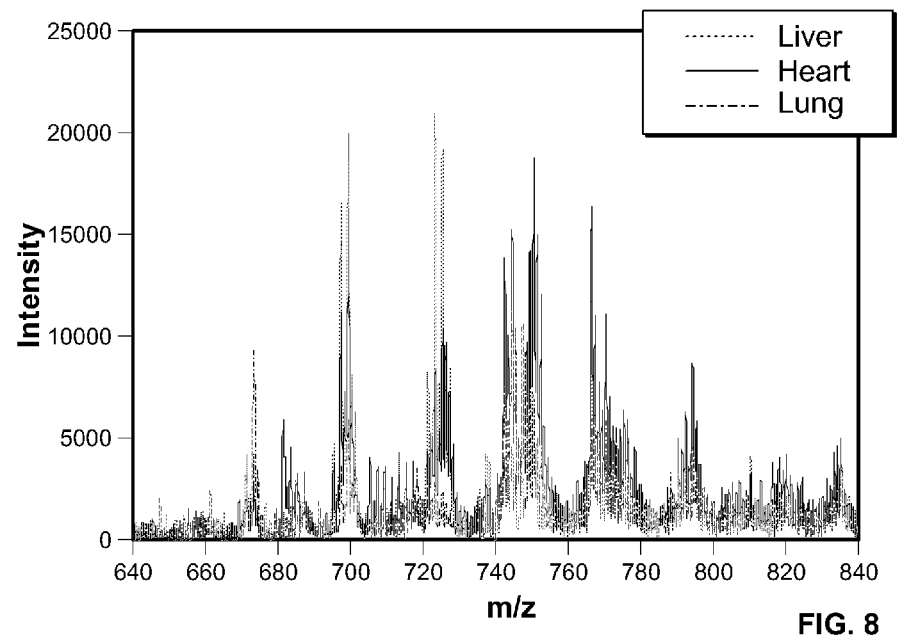
FIG. 8 illustrates mass spectra obtained from porcine liver, heart and lung in negative ion mode, during the electrosurgical dissection of corresponding organs using the setup depicted on FIG. 1.

Fluid pump 220 transfers neutral particles 60 to post ionization device, where a fraction of molecules of neutral particles 60 is converted to gaseous ions and sampled by mass spectrometer together with the gaseous ions 50 arising from the tissue. Mass spectrometer 130 can be used to separate all gaseous ions with regard to their mass-to-charge ratio and detected separately. Result of mass spectrometric analysis is mass spectrum (shown in FIGS. 6-9). Since neutral particles 60 cannot be completely separated from charged particles 50 in the atmospheric interface of mass spectrometer, charged and neutral particles 50, 60 tend to form adducts in ion optics or analyzer region of mass spectrometer. This phenomenon is undesired, since it leads to poorly resolved mass spectra (FIG. 6). Activation of ions by means of collision with inert gas molecules or inert surfaces or absorption of photons can be advantageously used to eliminate ion-molecule complexes and obtain mass spectra with appropriate resolution, as shown on FIG. 7. Since mass spectra cannot per se be directly used for identification of tissues or detection of trace amounts of certain tissues in different tissue matrix, mass spectra tissue-related data has to be processed by data analysis system 230. Mass spectra can be converted to vector format, and identified based on comparison with a database or library of mass spectra records corresponding to a plurality of tissue types. Analysis is aimed at either identification of spectra taken from pure tissues, or detection of certain type of tissue in matrix of other tissues. Alternatively, relative concentration of well defined components can also be calculated from spectra.

Since mass spectrometric analysis of ions takes less than about 200 ms, and data analysis can take from about 100 to about 150 ms, information feedback according to aspects of the present invention can take less than 1 second, thereby providing real-time tissue identification.

Mass spectra of tissues feature mainly membrane lipid constituents which give a tissue-specific pattern. Accordingly, in one aspect of the present invention, full spectral information can be used for the unequivocal identification of tissues. The data analysis can be based on principal component analysis (PCA), where, during the surgery, a pre-defined PCA space is used to spare analysis time. PCA space can be calculated using spectral database containing about 10,000 (ten thousands) spectra presently.

Real time tissue identification can be obtained by comparing the real time tissue-related mass spectra with mass spectra of known tissue types. The real time tissue-related mass spectra can be compared to a library of mass spectra records corresponding to a plurality of known tissue types. The library of records should include spectra of all tissue types which can theoretically be sampled during a surgical intervention. In one aspect of the present invention, the library of records can include spectra converted to vectors which are noise filtered and reduced to a number of dimensions (for example from 300 dimension data to 60 dimension data) via, for example, PCA. The differentiation of tissues/organs in the library of records can be carried out with 60 dimensional linear discriminant analysis (LDA) for quantitative classification of the data. Real time classification of spectra can be performed by using the library and classifying the real time spectra. Classification can be done using, for example, Mahalanobis distances.

Figure 13:
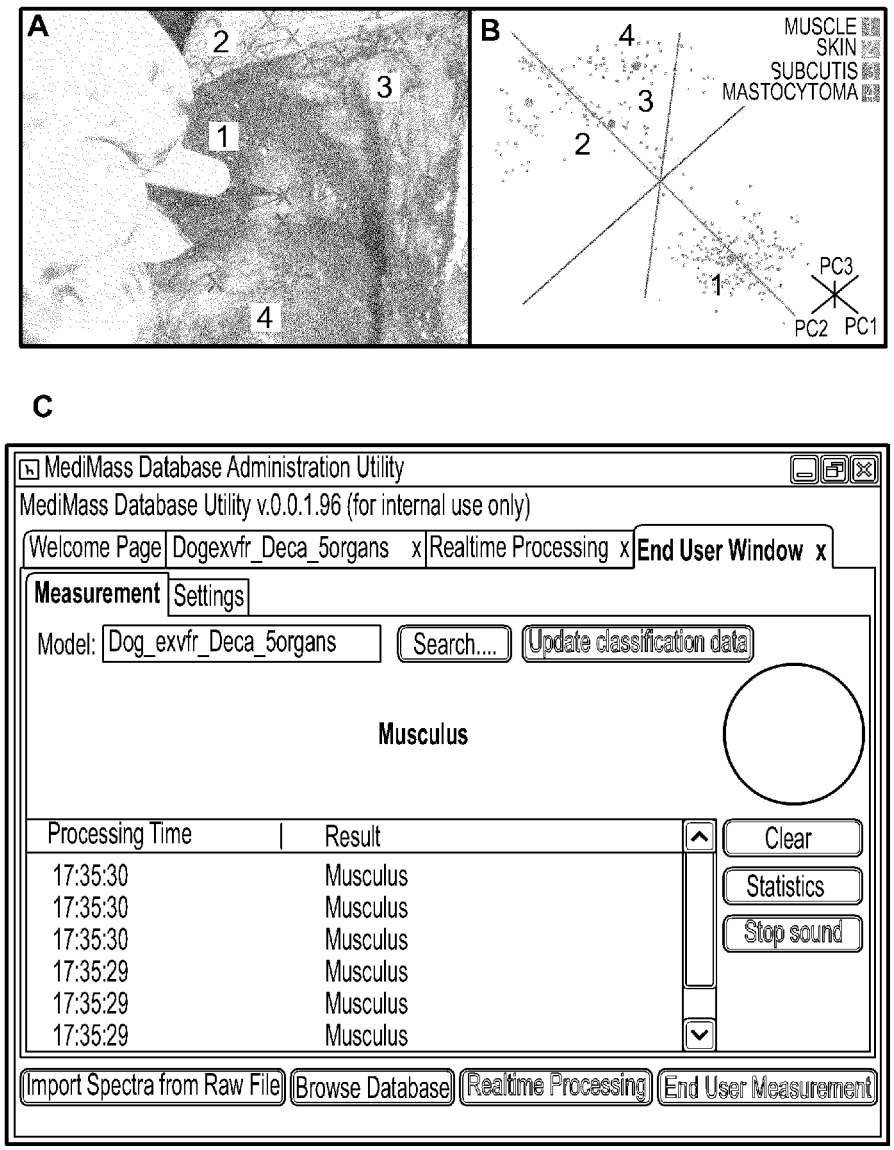
FIG. 13: panel A is a picture taken during a surgical dissection of a grade III mastocytoma in a dog, panel B is a three dimensional principal component analysis of the spectra taken from the marked places in panel a), and panel C is a screenshot of real time software during surgery of panel A. 1=muscle, 2=skin, 3=subcutis, 4=mastocytoma.

Analysis/localization/identification of the tissues using the devices, systems and methods of the present invention can be done in at least two different ways. In the so-called alerting mode the ionic species in the surgical aerosol can be continuously analyzed and the mass spectrometric system can give continuous feedback on the nature of the tissue being dissected. Screenshot of the graphical user interface of our software taken during surgery is shown on FIG. 13c. Whenever the result of the real-time spectral identification refers to the presence of malignant proliferation or whenever the identification of tissue fails, the system can give audiovisual alerting to the user of the system (i.e. a surgeon). An alternative way of utilization of the systems or methods of the present invention can be in the microprobe mode, when the tissue features of interest are sampled actively for the purpose of identification. From the perspective of mass spectrometric tissue identification, the main difference between the two modes is the data accumulation time for individual spectrum. While in the alerting mode data are accumulated for about 0.5-1 s, in microprobe mode the data for one spectrum are accumulated as long as the disintegrating device is generating gaseous tissue particles and collecting the gaseous tissue particles. In order to demonstrate the accuracy of intraoperational tissue identification, results obtained form individual sampling points (FIG. 13a) are shown in a two dimensional PCA plot (FIG. 13b).

Output information of data system can be continuously recorded and displayed on a feedback 240 device which may provide audio, visual or audiovisual information, if real-time analysis is needed. As a result, tissue parts in disintegrated volume 40 are analyzed and identified in an invasive manner, resulting in discontinuity 90 in tissue 20, 30. When discontinuity 90 is defined as a surgical cut, then the net analysis does not involve further invasiveness, compared to surgical cutting.

The present invention provides, in another aspect, a method of mass spectroscopy data acquisition characterized in that said method comprises: (a) generating a yield of gaseous charged particles from an area of interest in a sample (b) transporting the gaseous sample particles from the area of interest to a mass spectrometer, and (c) using the mass spectrometer for acquiring sample-related data based on the yield of gaseous sample ions from the area of interest. In one aspect of the present invention, the sample-related data can be made available through a database, including a library of mass spectra data records, for analysis or identification of biological tissue, including by medical personnel of a hospital or clinic.

EXAMPLES

The examples are described for the purposes of illustration and are not intended to limit the scope of the invention.

Example 1

Analysis and Identification of Tissue Parts During Surgery

By reference for example to FIG. 1, an electrosurgical unit (ICC 350, Erbe Elektromedizin GmbH) is used in combination with quadrupole ion trap mass spectrometer (LCQ Duo, ThermoFinnigan). Electrosurgical cutting electrode 10 was equipped with commercially available smoke removal unit 80 (Erbe), which was connected to fluid pump 220 (VAC 100, Veriflo) through 8⅛" OD 2 mm ID PTFE tubing. Fluid pump 220 was mounted on LCQ instrument using heavily modified DESI ion source (OmniSpray, Prosolia) platform. Mass spectrometer 130 was operated in negative ion mode. Ions in the range of 700-800 were isolated in ion trap, and were activated using collisional activation with neutral helium atoms. Spectra were acquired in range of m/z 700-800.

Canine in vivo and ex vivo data was acquired from dogs with spontaneous tumours from veterinary oncology praxis.

Figure 5:
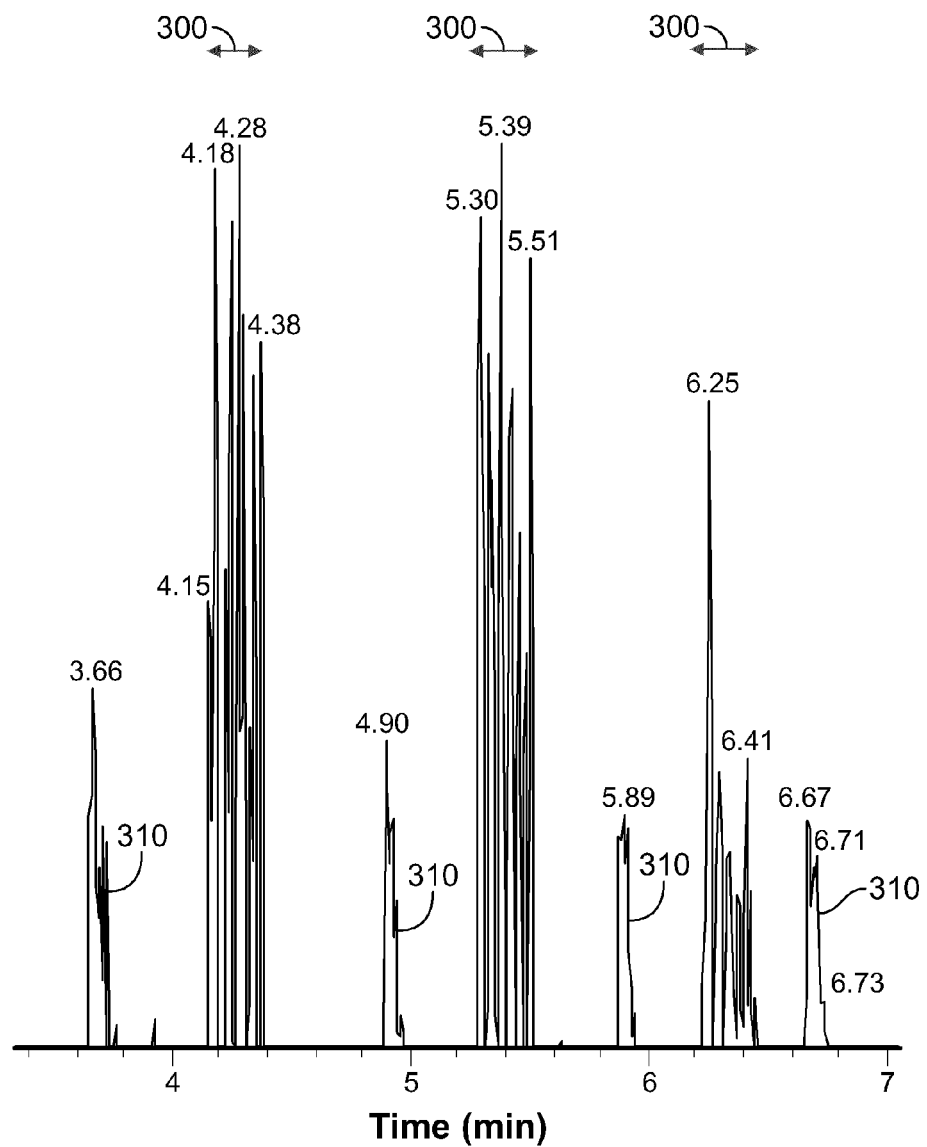
FIG. 5 illustrates total ion current obtained during application of device and method of the present invention in a surgical setting.
Figure 9:
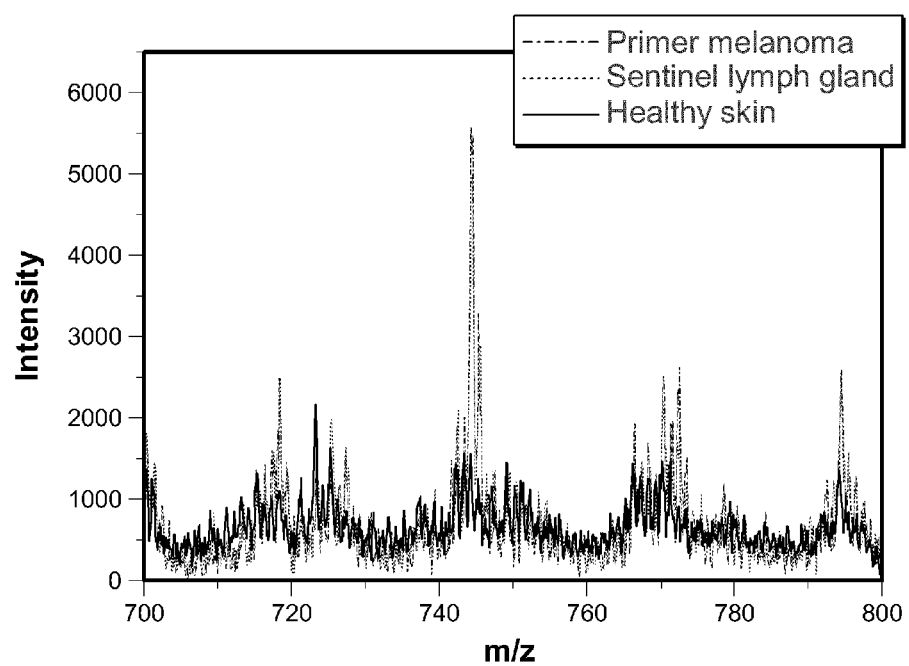
FIG. 9 illustrates mass spectra obtained from a canine melanoma, its proximal lymph node and surrounding healthy skin, in negative ion mode during electrosurgical removal of tumour and sentinel lymph node, using the setup depicted on FIG. 1.
Figure 10:
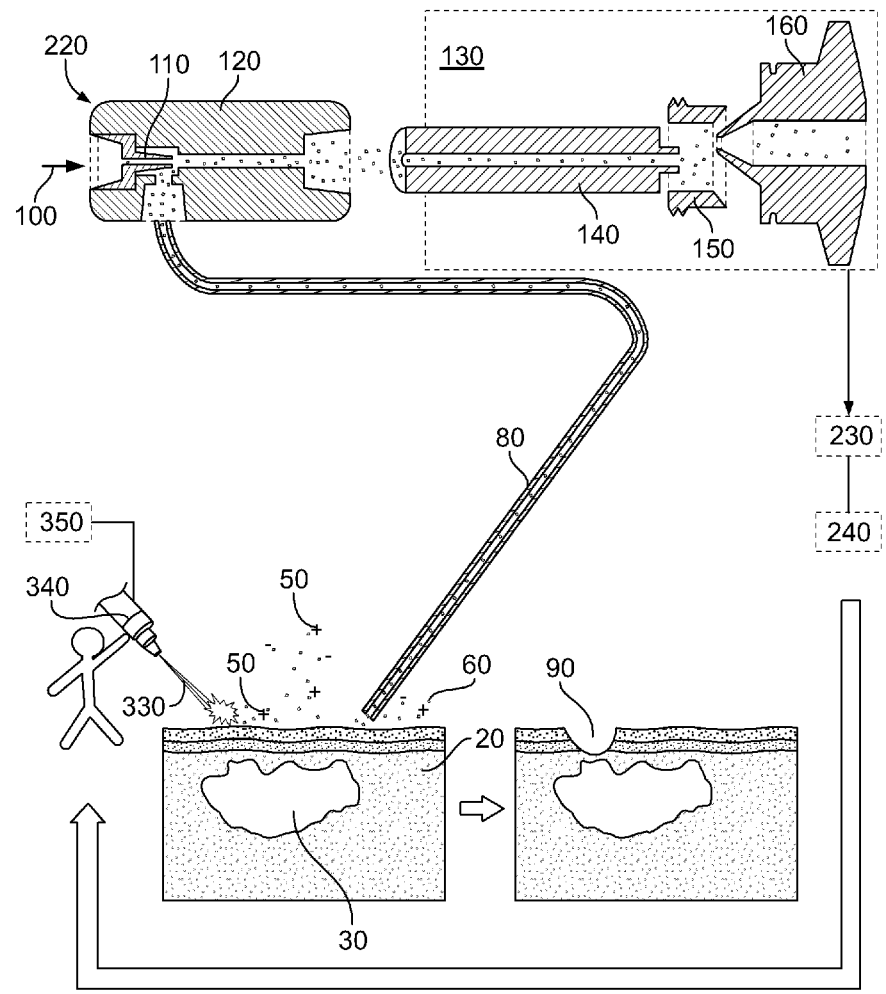
FIG. 10 illustrates a scheme of an in vivo mass spectrometric tissue identification method and device using laser means for creating gaseous tissue particles in accordance with yet another aspect of the invention.

Electrosurgical electrode 10 was used to remove malignant melanoma tumour 30 from healthy epithelial tissue 20, of the canine model. Tumour 30 was cut out together with parts of healthy skin 20 and surrounding lymph nodes carrying metastases, in order to minimize the chance for tumour recurrence. Tumour margin was determined based on mass spectrometric identification of tissue being cut. Mass spectrum of total ion current obtained during surgical intervention is shown in FIG. 5. Cutting periods during surgery are labelled as 300 and washing periods are labelled 310. It is important to point out, that mass spectrometric signals are detectable only when actual surgical cutting is performed 300 and during washing periods 310 when instrument is cleaned. Since both signal rise and fall times are extremely short compared to time of actual electrosurgical cutting, the experimental setup allows real-time analysis of tissues being cut, with minimized memory effects. Mass spectra taken from healthy epithelial tissue, melanoma and metastasis are shown in FIG. 9. Ratio of ions at m/z 746 and m/z 723 was used as tumour marker and this quantity was displayed on feedback device 240 translated to blue-red color gradient. Audio signal was also used as feedback, when frequency of beeping sound was changed as ion ratio was changed in MS spectra.

Tumour 20 was successfully removed surgically, and post-surgical histological examination of removed material has proven that surgery was successful, and removed lymph node carried tumour cells.

Example 2

Determination of Drugs in Tissues for Localization of Tumour Cells

An electrosurgical unit (ICC 350, Erbe Elektromedizin GmbH) is used in combination with quadrupole ion trap mass spectrometer (LCQ Duo, ThermoFinnigan). Electrosurgical cutting electrode 10 was equipped with commercially available smoke removal unit 80 (Erbe), which was connected to fluid-pump 220 (VAC 100, Veriflo) through 8⅛" OD 2 mm ID PTFE tubing. Fluid pump 220 was mounted on LCQ instrument using heavily modified DESI ion source (OmniSpray, Prosolia) platform. Fluid pump 220 was equipped with secondary electrospray post-ionization unit, comprising capillary 180 and high voltage power supply 170. Electrospray 260 and mass spectrometer 130 were operated in positive ion mode. Ions at m/z 447 and 449 were monitored with m/z 446 as background signal.

Nude mice carrying NCI-H460 human non-small cell lung cancer xenograft were house in a temperature- and light-controlled room, feed and water were supplied ad libitum. At age of 8 weeks, the mice were dosed with 2×20 mg/bw kg gefitinib. Following 3 days of drug treatment, tumour xenografts were sampled in vivo, under phenobarbital anesthesia.

Electrosurgical electrode 10 was used to remove 30 non-small cell lung cancer tumour from 20 healthy lung tissue of the murine model. Animals were subjected to pre-operational chemotherapy using Gefitinib. Gefitinib (molecular weight is 446) selectively binds to epithelial growth factor receptor (EGFR), which is overexpressed by NSCLC tumour cells. Thus, gefitinib can be used for the chemical labeling of these tumours. Molecular ions of gefitinib were monitored to localize infiltrating tumours.

Tumour 20 was cut out together with parts of 20 healthy lung tissue. Tumour margin was determined based on mass spectrometric identification of tissue being cut. Ratio of ions at m/z 447 and m/z 446 was used as tumour marker and this quantity was displayed on feedback device 240 translated to blue-red color gradient. Audio signal was also used as feedback, when frequency of beeping sound was changed as ion ratio was changed in MS spectra.

Tumour 20 was successfully removed surgically, and post-surgical histological examination of removed material has proven that surgery was successful.

Example 3

Localization and Identification of Bacterial Infections on Mucous Membranes

Home built thermal tissue disintegration device comprising DC power supply 70 and metal electrodes 10 is used in combination with quadrupole ion trap mass spectrometer (LCQ Duo, ThermoFinnigan). Metal electrodes 10 were connected to fluid pump 220 (VAC 100, Veriflo) through 8⅛" OD 2 mm ID PTFE tubing. Fluid pump 220 was mounted on LCQ instrument using heavily modified DESI ion source (OmniSpray, Prosolia) platform. Mass spectrometer 130 was operated in negative ion mode. Ions in the range of 640-840 were isolated in ion trap, and were activated using collisional activation with neutral helium atoms. Spectra were acquired in range of m/z 640-840.

Electrodes 10 were used to sample upper epithelial layer of mucous membranes infected by various bacteria. Since present application of method and device is aimed at minimally invasive analysis of mucous membranes, about 0.1-0.4 mg of total material comprising epithelial cells, bacteria, and mucus was disintegrated for recording one fully interpretable mass spectrum. Tissue part 20 (laryngeal mucous membrane) in contact with electrodes 10 was heated up to 850° C. Full mass spectra were compared to database comprising of mass spectra of 122 bacterial strains. Spectral similarity was defined as cosinus of 200 dimensional mass spectral data vectors. *Pseudomonas aeruginosa*, *Klebsiella pneumoniae*, *Staphylococcus aureus*, and *Streptococcus pneumoniae* were successfully identified, with the appropriate data entry at the first position of database search hit list. In most of the cases, the first three hits also belonged to the same genus.

Example 4

Business Model

Figure 12:
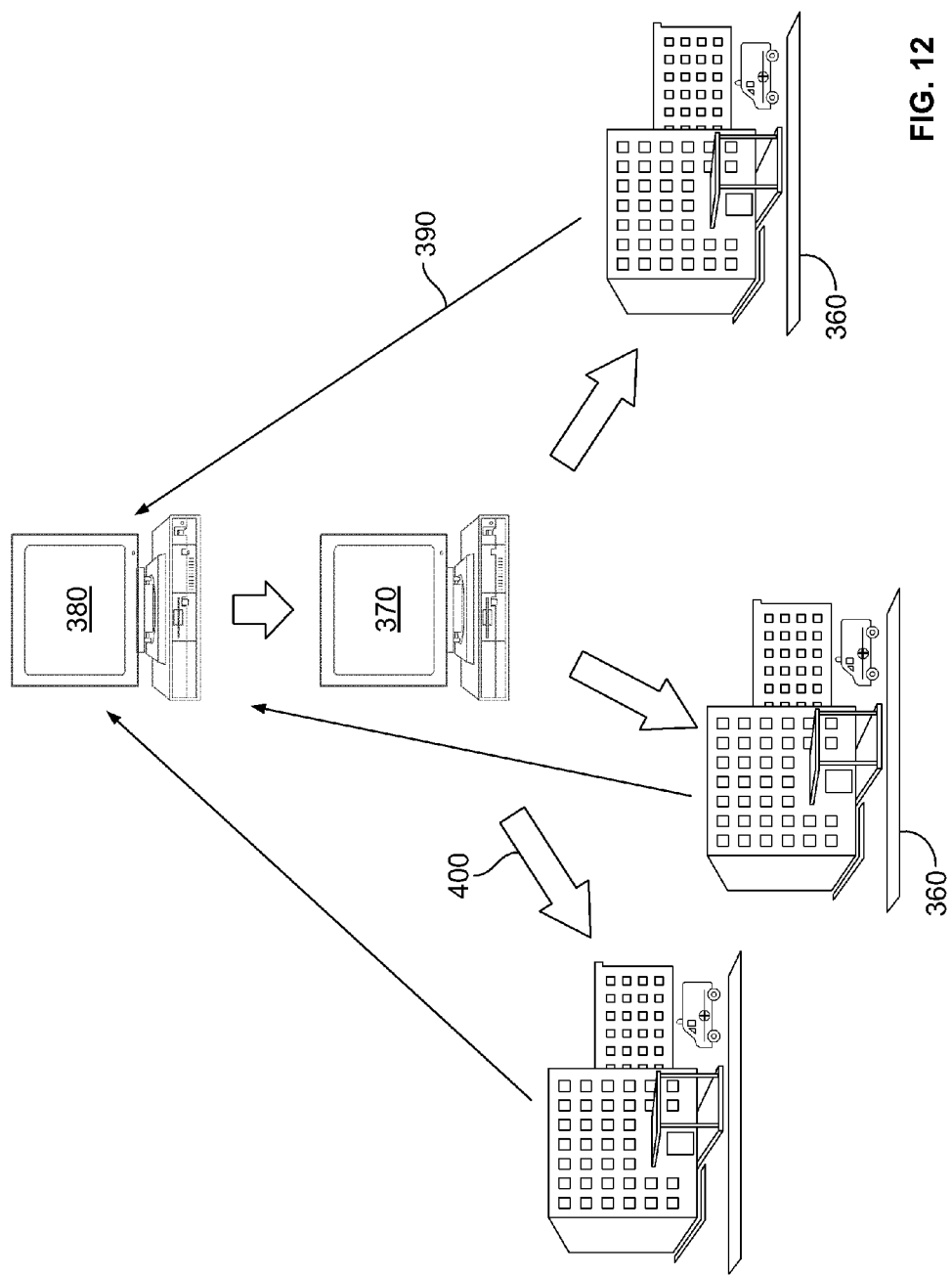
FIG. 12 illustrates a scheme of data flow between hospitals and database development unit. Hospitals facilitate database development by providing the manufacturer with raw, histologically assigned data, while the manufacturer processes the data and stores it in a central database.

The present invention includes four main identified application areas: robotized surgery, general oncosurgery, pathology and microbial diagnostics. Since price range of instruments used in everyday practice is considerably lower than market price of mass spectrometric systems, the mass spectrometer part of the present invention can be sold to clinics, pathology labs, outpatient offices etc. at net cost of manufacturing. Actual profit can be realized by making parts 10, 80, 220, and post-ionization devices as single-use consumable parts of the system of the invention. This can be a desirable feature because otherwise these parts 10, 80, 220 need to be thoroughly cleaned and disinfected after each surgical or diagnostic intervention. Further possible source of profit can be the software used for interpretation of data and identification of individual mass spectra. Both search engine and database can be continuously developed and sold to users for a low, but recurrent fee. All sold systems can be linked to an internet-based network, which continuously provides the development team 380 with raw data 390, and facilitates the development of central tissue spectrum database 370 as it is depicted on FIG. 12. Hospitals 360 can receive fully uniformized and reliable data 400 via internet.

The above disclosure generally describes the present invention. Changes in form and substitution of equivalents are contemplated as circumstances may suggest or render expedient. Although specific terms have been employed herein, such terms are intended in a descriptive sense and not for purposes of limitation. Other variations and modifications of the invention are possible. As such modifications or variations are believed to be within the sphere and scope of the invention as defined by the claims appended hereto.

What is claimed is:

1. A method for analyzing tissue during a surgical procedure, the method comprising:
    touching the tissue with a disintegrating device to disintegrated a portion of the tissue in situ during a surgical procedure and generate gaseous tissue particles from a site in the tissue wherein the disintegrating device operates by at least one of: ultrasonication, Joule-heating, and contact heating;
    transporting the gaseous tissue particles away from the site;
    ionizing at least a portion of the gaseous tissue particles away from the site to generate gaseous sample ions; and
    using an analyzer to generate tissue-related data based at least on the gaseous sample ions.

2. The method of claim 1, wherein said gaseous tissue particles comprise at least one of: individual molecules in gas phase, and clusters of molecules.

3. The method of claim 1, wherein disintegrating the portion of tissue is performed in vivo.

4. The method of claim 1, wherein the analyzer comprises one of: a mass spectrometer and an ion mobility spectrometer.

5. The method of claim 1, wherein said ionizing is performed by an ionization device incorporated into a fluid pump that induces a pressure gradient in a transport tube that transports the gaseous tissue particles away from the site.

6. The method of claim 5, wherein said ionizing comprises one of: corona discharge ionization and secondary electrospray ionization.

7. The method of claim 1, further comprising signaling the results of the analysis to a user in real time.

8. The method of claim 7, wherein said signaling is continuously displayed to the user.

9. The method of claim 1, further comprising comparing said tissue-related data with a library of data corresponding to a plurality of known tissue types.

10. A system for analyzing tissue during a surgical procedure, the system comprising:
   a disintegrating device configured to touch the tissue so as to disintegrate a portion of tissue in situ during a surgical procedure to generate gaseous tissue particles from a site in the tissue wherein the disintegrating device operates by at least one of: ultrasonication, Joule heating, and contact heating;
   a transport tube configured to transport the gaseous tissue particles away from the site;
   an ionizing device configured to ionize at least a portion of the gaseous tissue particles away from the site to generate gaseous sample ions; and
   an analyzer for generating tissue-related data based at least on the gaseous sample ions.

11. The system of claim 10, wherein the gaseous tissue particles comprise at least one of: individual molecules in gas phase, and clusters of molecules.

12. The system of claim 10, wherein the disintegrating device is capable of generating gaseous tissue particles from a portion of tissue in vivo.

13. The system of claim 10, wherein the analyzer comprises one of: a mass spectrometer and an ion mobility spectrometer.

14. The system of claim 10, wherein the ionizing device is incorporated into a fluid pump that induces a pressure gradient in the transport tube.

\* \* \* \* \*

UNITED STATES PATENT AND TRADEMARK OFFICE
CERTIFICATE OF CORRECTION

| | | |
|---|---|---|
| PATENT NO. | : 9,046,448 B2 | Page 1 of 1 |
| APPLICATION NO. | : 13/322343 | |
| DATED | : June 2, 2015 | |
| INVENTOR(S) | : Takats | |

It is certified that error appears in the above-identified patent and that said Letters Patent is hereby corrected as shown below:

In the specification

Column 14 line 44, Change "ton)" to --torr)--.

In the claims

Column 20 line 46, Claim 1, change "tissue" to --tissue,--.

Column 21 line 14, Claim 10, change "tissue" to --tissue,--.

Signed and Sealed this
Fifth Day of April, 2016

Michelle K. Lee
*Director of the United States Patent and Trademark Office*